United States Patent

Takubo et al.

[11] Patent Number: 6,061,466
[45] Date of Patent: May 9, 2000

[54] APPARATUS AND METHOD FOR INSPECTING AN LSI DEVICE IN AN ASSEMBLING PROCESS, CAPABLE OF DETECTING CONNECTION FAILURE OF INDIVIDUAL FLEXIBLE LEADS

[75] Inventors: Chiaki Takubo, Tokyo; Eiichi Hosomi, Kawasaki; Hiroshi Tazawa, Yokohama; Koji Shibasaki, Kawasaki, all of Japan

[73] Assignee: Kabushiki Kaisha Toshiba, Kawasaki, Japan

[21] Appl. No.: 08/773,054

[22] Filed: Dec. 24, 1996

[30] Foreign Application Priority Data

Dec. 26, 1995 [JP] Japan .................................. 7-339392

[51] Int. Cl.$^7$ ....................................................... G06K 9/00
[52] U.S. Cl. ........................... 382/146; 348/126; 382/150
[58] Field of Search .................................. 382/146, 150; 348/86, 90, 92, 125, 126

[56] References Cited

U.S. PATENT DOCUMENTS

| | | | |
|---|---|---|---|
| 5,249,239 | 9/1993 | Kida | 382/146 |
| 5,495,424 | 2/1996 | Tokura | 382/150 |
| 5,598,345 | 1/1997 | Tokura | 382/150 |
| 5,901,241 | 5/1999 | Koljonen et al. | 382/150 |
| 5,909,285 | 6/1999 | Beaaty et al. | 382/146 |

*Primary Examiner*—Joseph Mancuso
*Attorney, Agent, or Firm*—Finnegan, Henderson, Farabow, Garrett & Dunner, L.L.P.

[57] ABSTRACT

Disclosed is an apparatus and method for inspecting a connection state of a lead electrode to a bump after TAB (tape automated bonding). An LSI chip is immobilized on a stage. A flexible lead is held by a holding portion and connected to a bump. Above the chip, a CCD camera is provided. The stage is controlled to move up and down by a moving control mechanism. Each of the lead/bump connection states immediately after ILB (Inner lead bonding) is taken in the form of image data and defined as a first image data. A second image data of the lead/bump connection state is taken after the bump and lead are moved to different positions by moving the stage in order to change the position of the chip by means of the moving control mechanism. Whether or not the lead is duly connected to the bump is determined by the comparison of the first and second image data.

15 Claims, 6 Drawing Sheets

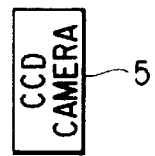
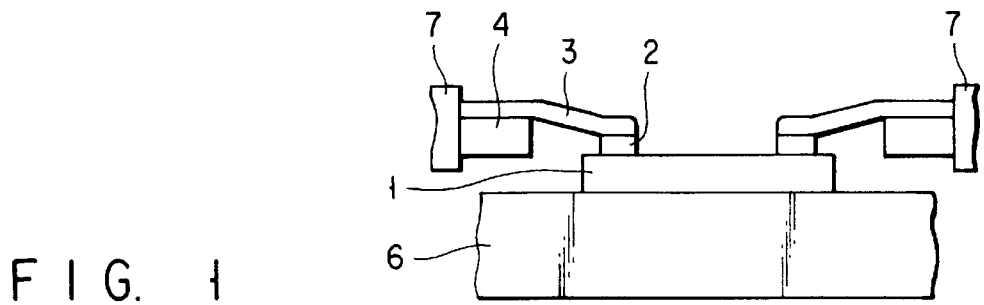
FIG. 1
FIG. 2
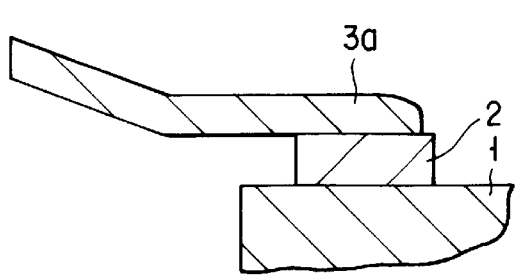
FIG. 3
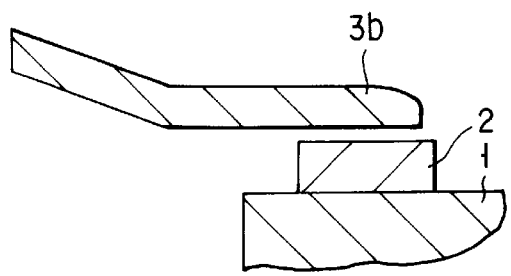
FIG. 4

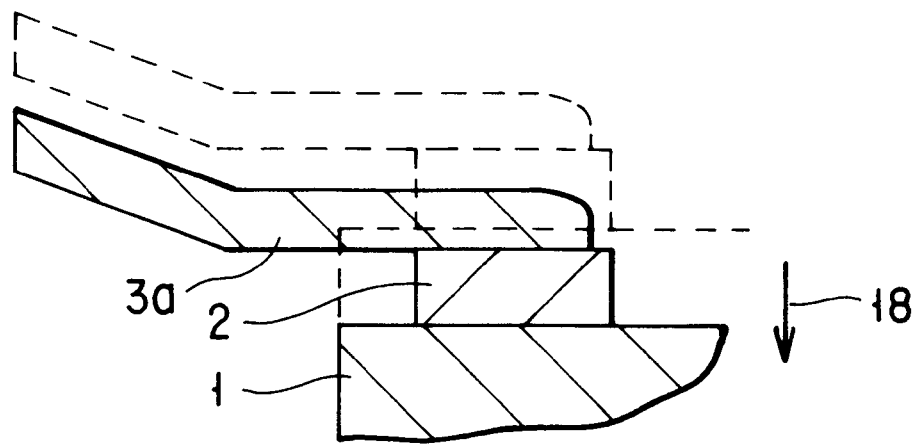
F I G. 11
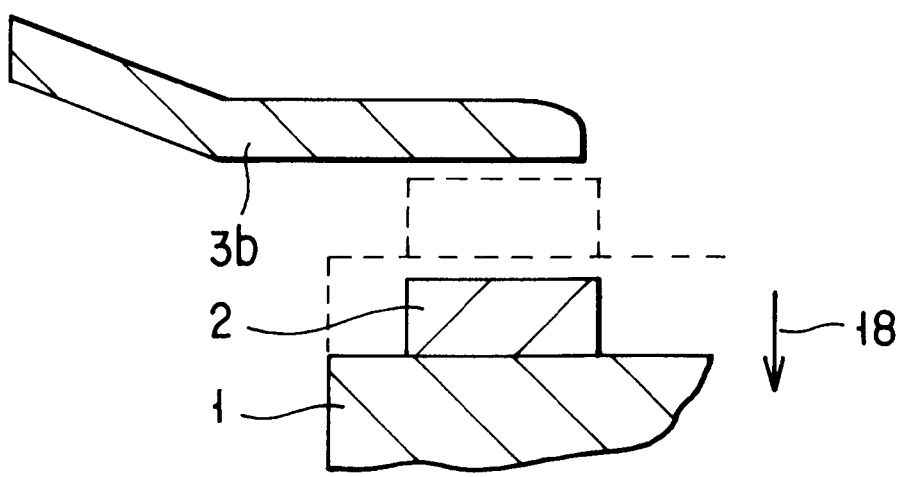
F I G. 12

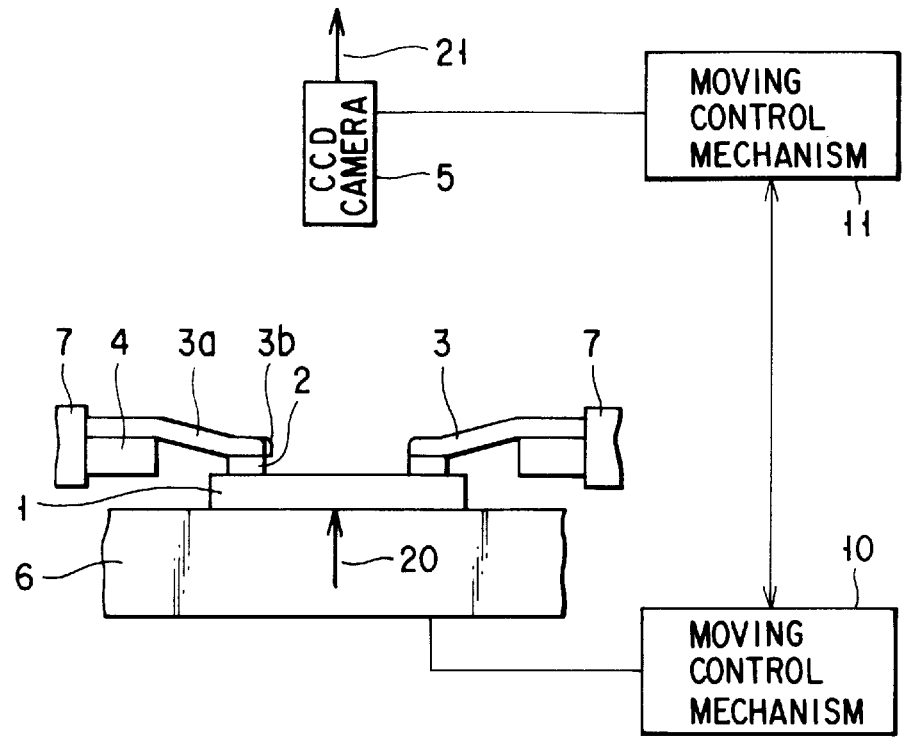
F I G. 13
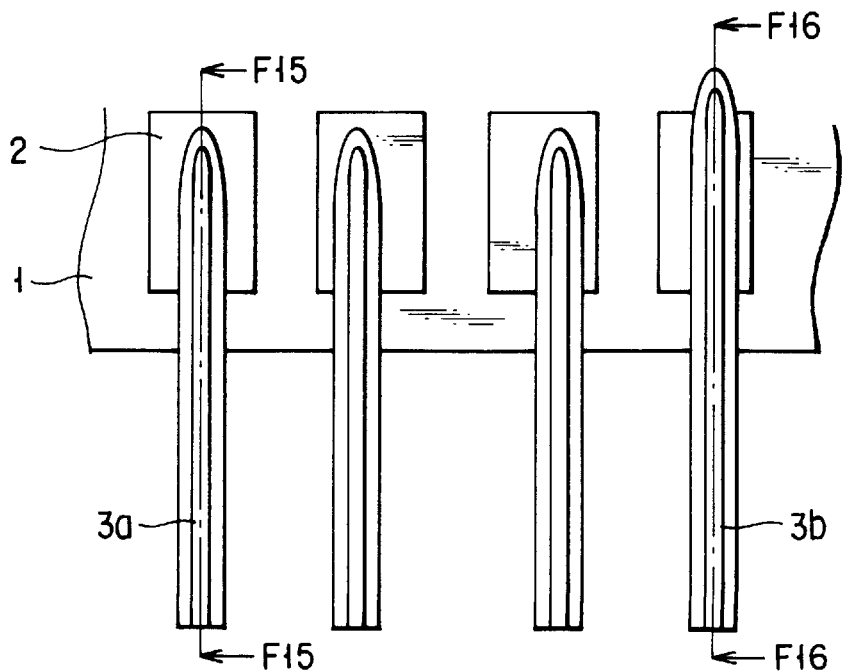
F I G. 14

APPARATUS AND METHOD FOR INSPECTING AN LSI DEVICE IN AN ASSEMBLING PROCESS, CAPABLE OF DETECTING CONNECTION FAILURE OF INDIVIDUAL FLEXIBLE LEADS

BACKGROUND OF THE INVENTION

The present invention relates to an apparatus and method for inspecting a connection state of a lead electrode to a bump after the lead electrode is bonded to the bump on an LSI chip. The apparatus and method of the present invention are used in a TAB (tape automated bonding) employed in assembling an LSI chip.

The inner leads (hereinafter referred to as "leads") of an LSI chip are inspected to establish whether or not they are duly connected to the corresponding bumps after the inner lead bonding (ILB). The ILB profile is taken by a CCD camera in the form of image data and the positions of the bump and the lead are determined in the image data. In this way, an out of place of the lead from the right contact position can be detected.

FIG. 1 is a side view of a conventional apparatus for inspecting an LSI device in the assembly process, by which the aforementioned inspection is carried out. A thin flexible lead 3 is formed on a pliable film 4 (sometimes referred to as "TAB tape") and is connected to a bump 2 formed on an LSI chip 1. The chip 1 is immobilized on a stage 6 by means of vacuum adsorption. A holding portion 7 holds the film 4 attached with the lead 3. Above the chip 1, a CCD camera 5 is provided which is used in confirming the positions of the lead and the bump. The CCD camera 5 takes a picture of the connecting portion of the bump to the lead, magnifies, and incorporates it in the form of image data.

The camera 5 takes the image data by placing focus on the upper surface of the bump or of the lead. If the upper bump surface is brought into focus, the upper lead surface automatically comes into focus, since the camera has a predetermined depth of focus. Conversely, if the upper lead surface is brought into focus, the upper bump surface comes into focus. After the image data is taken, the bump and the lead figures are checked to determine whether or not the lead slips from the bump. In this manner, it is possible to detect the out of place of the lead from the right contact position after the ILB.

However, when the lead is just in touch with the bump or when the lead is separated slightly from the bump in an upward direction, causing a connection failure, it is difficult to determine whether or not the lead is duly connected to the bump, from the image data taken by the camera 5.

FIG. 2 represents part of the image data taken by the CCD camera shown in FIG. 1, showing a lead/bump connection state. The longitudinal cross section of the lead 3 (3a, 3b) is a trapezoid, the upper side of which is shorter than the lower side (not shown). When the lead 3 (3a, 3b) is viewed from the above, only the upper surface and taper surfaces are seen, as shown in FIG. 2.

FIG. 3 and FIG. 4 are cross-sectional views taken along line F3—F3 and line F4—F4 of FIG. 2, respectively. In FIG. 3, the lead 3a is duly connected to the bump 2. In FIG. 4, the lead 3b is slightly separated from the bump 2, causing a connection failure. However, such connection failure cannot be detected by the conventional method since both lead 3b and bump 2 are in focus by virtue of the depth of focus inherent in the camera 5, as is evidenced in FIG. 2.

BRIEF SUMMARY OF THE INVENTION

The object of the present invention is to provide an apparatus and method for inspecting an LSI device in the assembly process, capable of detecting a connection failure including a slight upward separation of a lead, from image data taken by a camera.

The object of the present invention can be achieved by the apparatus and method described below.

An apparatus for inspecting an LSI device in the assembly process, comprising:

a stage for immobilizing an LSI chip thereon, an assembly mechanism for controlling a lead so as to be connected to a predetermined portion of the LSI chip; and an image-data receiving mechanism for taking at least two types of image data: one is an image data of the lead connection state immediately after the connection is made by the assembly mechanism and the other is an image data of the lead connection state after the lead is moved to a different position.

The method for inspecting an LSI device in the assembly process comprising the steps of:

assembling an LSI chip by controlling a flexible lead to be connected to a bump of the LSI chip;

taking a first image data by a camera, which is an image data of the lead/bump connection state obtained immediately after the assembling;

taking a second image data by a camera, which is an image data of the lead/bump connection state after the distance between the chip and the camera is changed; and determining whether or not the lead is duly connected to the bump by comparing the first image data to the second image data.

According to the present invention, it is possible to detect whether or not the lead is duly connected to a predetermined portion of the LSI chip by finding out-of-focus image data through the comparison of two types of image data to each other.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a side view of a conventional apparatus for inspecting an LSI device in the assembly process;

FIG. 2 represents part of the image data taken by the CCD camera shown in FIG. 1, showing a lead/bump connection state;

FIG. 3 is a cross-sectional view taken along line F3—F3 of FIG. 2;

FIG. 4 is a cross-sectional view taken along line F4—F4 of FIG. 2;

FIG. 11 is a cross-sectional view taken along line F11—F11 of FIG. 10;

FIG. 12 is a cross-sectional view taken along line F12—F12 of FIG. 10;

FIG. 13 is a side view of the apparatus for inspecting an LSI device in the assembly process according to Embodiment 3 of the present invention;

FIG. 14 represents part of a second image data taken by the CCD camera shown in FIG. 13, showing a lead/bump connection state;

DETAILED DESCRIPTION OF THE INVENTION

Figure 5:
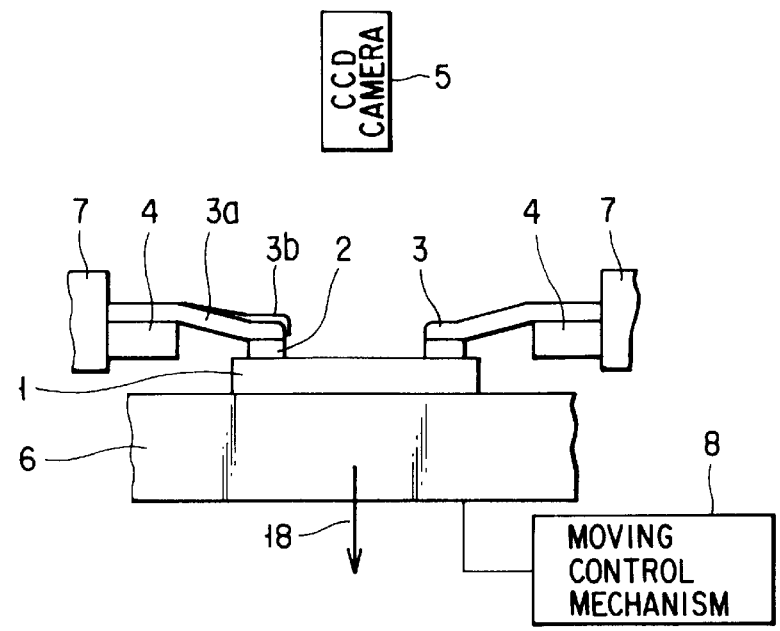
FIG. 5 is a side view of the apparatus for inspecting an LSI device in the assembly process according to Embodiment 1 of the present invention.

FIG. 5 is a side view of the apparatus for inspecting an LSI device in the assembly process according to Embodiment 1 of the present invention. An LSI chip 1 is fixed on a stage 6 by means of vacuum adsorption. A flexible lead 3 (3a, 3b) is formed on a pliable film 4 and connected to a bump 2 formed on the LSI chip 1. The film attached with the lead 3 is held by a holding portion 7. Above the LSI chip 1, a CCD camera 5 is provided. The stage 6 is controlled to move up and down by means of a moving control mechanism 8.

After the inner lead bonding (ILB) step in which individual bumps 2 are connected to the corresponding leads 3, a camera 5 takes the connection states of the leads 3 to the bumps 2 in the form of image data. In the present invention, the connection state of the leads 3 to the bumps 2 immediately after the ILB, is taken as a first image data. After the positions of the lead and bump are changed by moving, for example, the stage 6, slightly in a downward direction to thereby move only the LSI chip, the image data of the lead/bump connection state is taken as a second image data. The movement of the stage 6 is controlled by means of the moving control mechanism 8 so as to move by a predetermined distance in the direction indicated by an arrow 18 shown in FIG. 5

Figure 6:
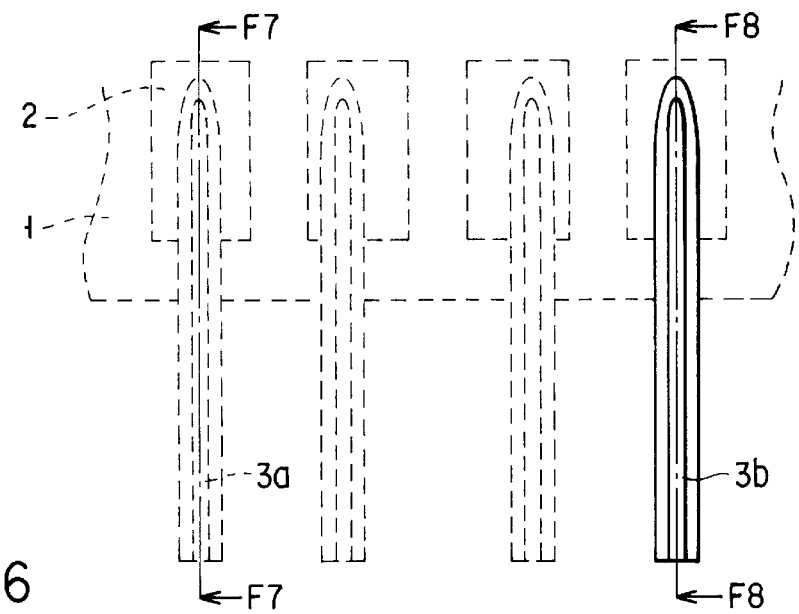
FIG. 6 represents part of a second image data taken by the CCD camera shown in FIG. 5, showing a lead/bump connection state.

FIG. 6 represents part of a second image data taken by the camera 5 shown in FIG. 5, showing a lead/bump connection state. The longitudinal cross-section of the lead 3 (3a, 3b) is a trapezoid the upper side of which is shorter than the lower side (not shown). When the lead 3 is viewed from the above, only the upper surface and taper surfaces are seen, as evidenced in FIG. 6.

Figures 7, 8:
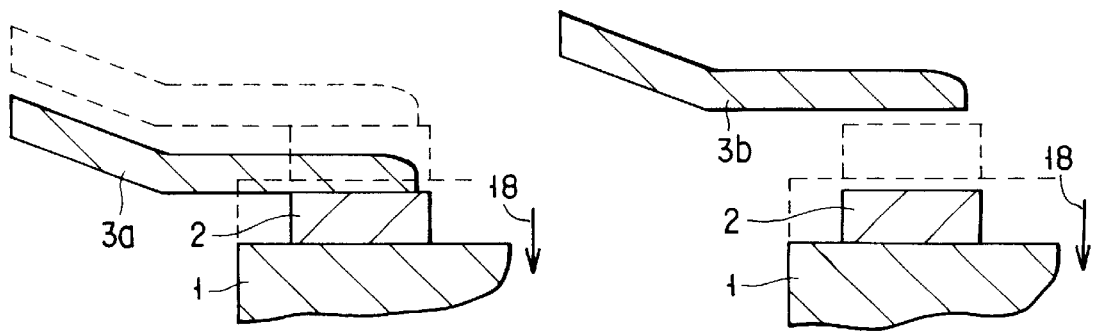
FIG. 7 is a cross-sectional view taken along line F7—F7 of FIG. 6.
FIG. 8 is a cross-sectional view taken along line F8—F8 of FIG. 6.

FIG. 7 and FIG. 8 are cross-sectional views taken along line F7—F7 and line F8—F8 of FIG. 6, respectively. In FIG. 7, the lead 3a is duly connected to the bump 2. In FIG. 8, the lead 3b is slightly separated from the bump 2 in an upward direction, causing a connection failure.

As is mentioned in the above, after the fist image data is taken immediately after the ILB, the stage 6 is moved down along the arrow 18 by means of the moving control mechanism 8 while the film 4 attached with the lead is left in the original position. As a result, the lead 3a duly connected to the bump 2 is moved together with the chip 1, as shown in FIG. 7. However, the lead 3b not duly connected to the bump 2 is left in the original position, as shown in FIG. 8 (also shown in FIG. 5).

When the second image data of such a connection state is taken after the movement, the lead 3b separated slightly from the bump 2 is still in focus exactly the same as at the time the first image data is taken, whereas the lead 3a duly connected to the bump 2 is out of focus, creating a fuzzy image, as shown in the image data of FIG. 6. In short, the not-duly connected lead 3b can be recognized, whereas the duly-connected lead 3a to bump 2 cannot.

According to the aforementioned method, it is possible to determine that the connection failure is present in the lead (3) whose image can be recognized even after the chip 1 is moved down. In this manner, a failure in the lead connection can be accurately and readily detected. Note that the moving distance of the chip 1 should be larger than the depth of focus inherent in the camera 5.

The depth of focus varies with the magnification of a camera to be used. Generally, the depth of focus is reduced with an increase in the magnification. If the depth of focus is shallow, the lead connected to the bump is out of focus even if the moving distance of the chip is small. However, if the depth of focus is extremely shallow, it is difficult even to capture the image itself. For example, when the upper surface of the lead is brought into focus, the upper surface of the bump does not come into focus. Alternatively, if the upper surface of the bump is brought into focus, the upper lead surface does not come into focus. To circumvent such a problem, it is preferable that the camera 5 have an appropriate magnification enough to recognize the image.

Figure 9:
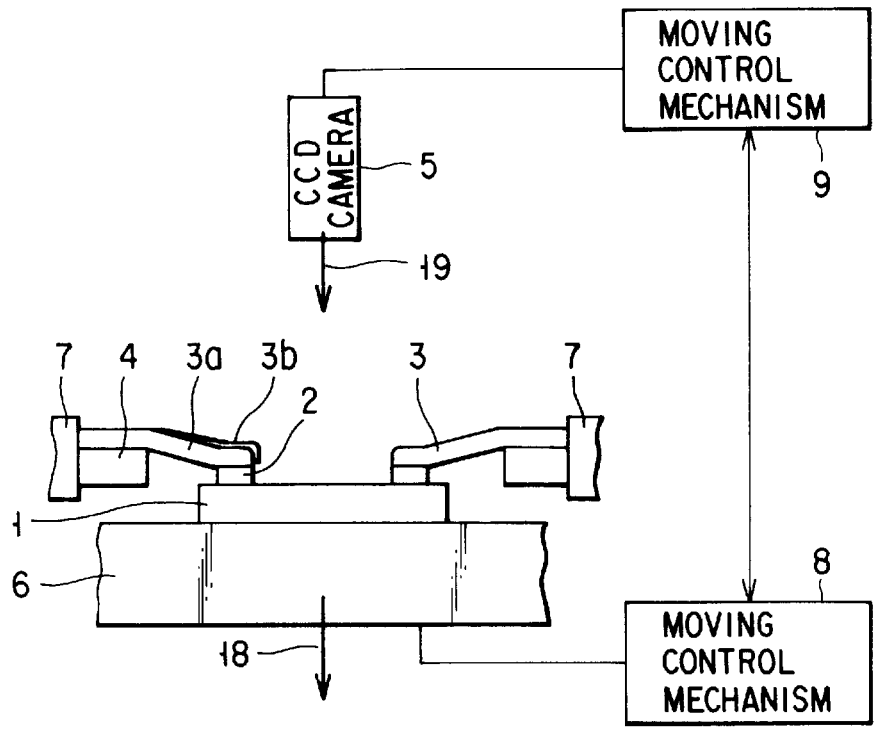
FIG. 9 is a side view of the apparatus for inspecting an LSI device in the assembly process according to Embodiment 2 of the present invention.

FIG. 9 is a side view of the apparatus for inspecting an LSI device in the assembly process according to Embodiment 2 of the present invention. The different point from Embodiment 1 resides in that a stage 6 is moved down in the direction of an arrow 18 (FIG. 9) by means of a moving control mechanism 8; at the same time, a camera 5 is moved down in the direction of an arrow 19 (FIG. 9) by the same distance by means of a moving control mechanism 9, for taking the second image data. By this operation, the chip 1 and the camera 5 after the movement are controlled to maintain the same distance before the movement.

Figure 10:
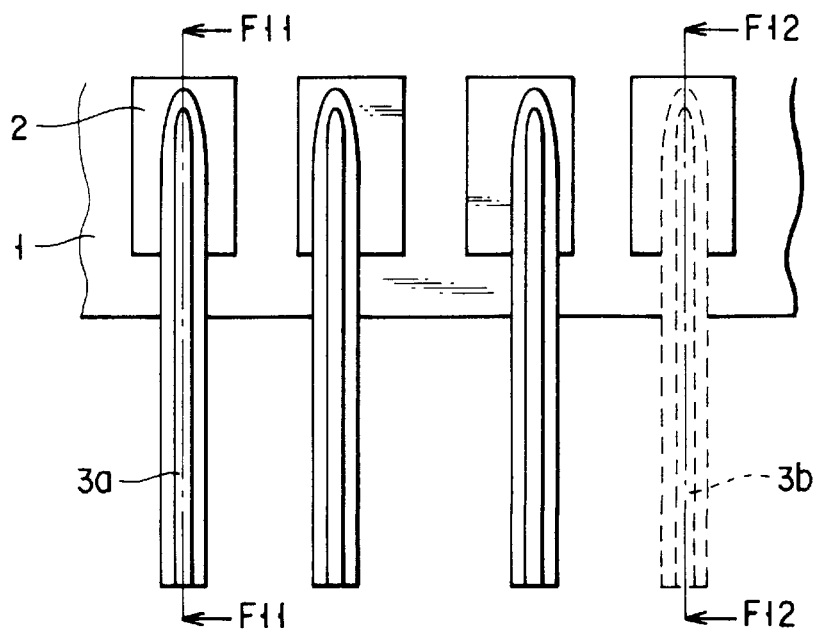
FIG. 10 represents part of a second image data taken by the CCD camera shown in FIG. 9, showing a lead/bump connection state.

FIG. 10 represents part of a second image data taken by the camera shown in FIG. 9, showing a lead/bump connection state. FIG. 11 and FIG. 12 are cross-sectional views taken along line F11—F11 and line F12—F12 of FIG. 10, respectively. In FIG. 11, the lead 3a is duly connected to the bump 2. In FIG. 12, the lead 3b is separated slightly from the bump 2 in an upward direction, causing a connection failure.

To describe more specifically, after the first image data is taken immediately after the ILB, the stage 6 is moved down in the direction of the arrow 18 by means of the moving control mechanism 8 while the film 4 with the lead is left in the original position and simultaneously the camera 5 is moved down in the direction of the arrow 19 by the same distance by means of the moving control mechanism 9. After the movement, the chip 1 and the camera 5 keep the same distance before the movement.

As a result, the lead 3a duly connected to the bump 2 is moved down together with the chip 1, as shown in FIG. 11, whereas the lead 3b separated slightly from the bump 2, is left in the original position, as shown in FIG. 12 (also shown in FIG. 9).

When the second image data of such a bump/lead connection state is taken after the movement, the lead 3a duly connected to the bump 2 is still in focus exactly the same as at the time the first image data is taken, since the camera and the chip are moved by the same distance. However, the lead 3b separated slightly from the bump 2 is out of focus, creating a fuzzy image. Hence, it is difficult to recognize the lead 3b.

According to the aforementioned method, the connection failure is present in the lead (3) whose image cannot be recognized after the chip 1 is moved down. Therefore, In Embodiment 2, as is the same as in Embodiment 1, the slight upward separation of the lead can be accurately and readily detected by use of the out-of-focus image. It should be noted that the moving distance between the chip 1 and camera 5 is larger than the depth of focus of the camera 5, similarly to Embodiment 1. The depth of focus varies depending on the magnification of a camera to be employed. It is therefore preferable to chose a camera having an appropriate magnification enough to recognize the image.

FIG. 13 is a side view of the apparatus for inspecting an LSI device in the assembly process according to Embodiment 3 of the present invention. The point different from Embodiment 1 resides in that a stage 6 is moved in the direction of an arrow 20 by means of a moving control mechanism 10 and simultaneously a camera 5 is moved up in the direction of an arrow 21 by the same distance by means of a moving control mechanism 11, for taking the second image data after the ILB. Since the chip 1 and the camera 5 are moved synchronously after the first image data is taken, the chip 1 and the camera 5 after the movement maintain the same distance as that at the time the first image is taken.

Figure 15:
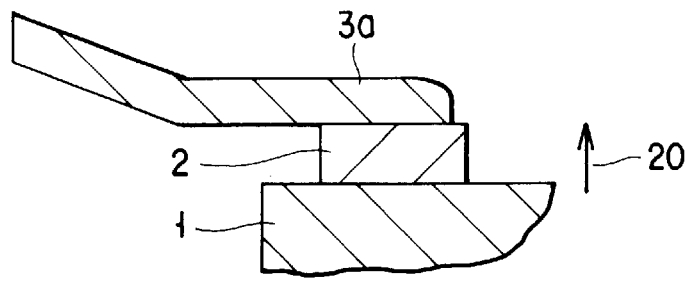
FIG. 15 is a cross-sectional view taken along line F15—F15 of FIG. 14.
Figure 16:
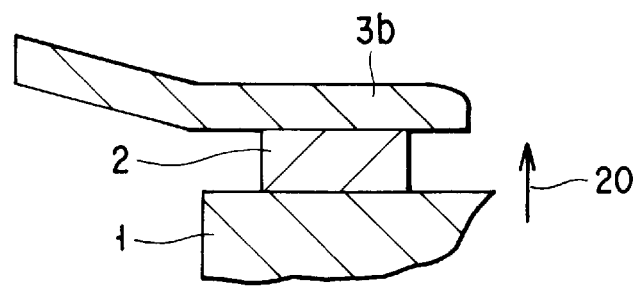
FIG. 16 is a cross-sectional view taken along line F16—F16 of FIG. 14.

FIG. 14 represents part of a second image data taken by the camera 5 shown in FIG. 13, showing a lead/bump connection state. FIG. 15 and FIG. 16 are cross-sectional views taken along line F15—F15 and line F16—F16 of FIG. 14. In FIG. 11, the lead 3a and the bump 2 are duly connected. However, in FIG. 12, the lead 3b is separated slightly from the bump in an upward direction, causing a connection failure.

To describe more specifically, after the first image data is taken immediately after the ILB, the stage 6 is moved up in the direction of an arrow 20 by means of the moving control mechanism 10 while the film 4 with a lead is left in the original position, and the camera 5 is simultaneously moved up in the direction of an arrow 21 by the same distance by means of the moving control mechanism 11. After the movement, the chip 1 and camera 5 keep the same distance before the movement.

As a result, the lead 3a duly connected to the bump 2 is moved up together with the tip 1, as shown in FIG. 15, causing no out of place in position. The lead 3b not duly connected to the bump 2 is also moved up together with the chip 1. In this case, however, an out of place in position occurs, as shown in FIG. 16 (also shown in FIG. 13 and FIG. 14).

When the second image data of such a lead/bump connection state is taken after the movement, the lead 3a duly connected to the bump 2 is still in focus, as is apparent from the image of the bump and lead shown in FIG. 14, since the camera and the chip are moved by the same distance. The lead 3a is retained in the same position as that at which the first data image is taken, detecting no out of place in position, whereas the out of place in position is observed in the lead 3b not duly connected to the bump 2 due to the slight upward separation.

In this method, it is determined that the connection failure is present in the lead causing the out of place in position after the chip 1 is moved up. In this manner, the connection failure due to slight upward separation can be detected accurately and readily.

According to Embodiments 1 to 3 explained in the foregoing, the connection failure due to slight upward separation after the ILB can be detected by using the camera which confirms the position. Hence, the connection failure due to slight upward separation after the ILB can be determined together with an out of place in position for a short time. When the leads having the connection failure are detected by any one of the methods shown in the aforementioned Embodiments, they are subjecting to the bonding (ILB) step followed by the inspecting step repeatedly. If so, defective products due to the connection failure will be significantly reduced, resulting in a great improvement in the assembly yield of an LSI device. As the image-taking camera for detection, the camera primarily used in setting positions for bonding may be used. Besides the position-setting camera, an additional camera may be used which exclusively serves as the image-taking camera.

Figure 17:
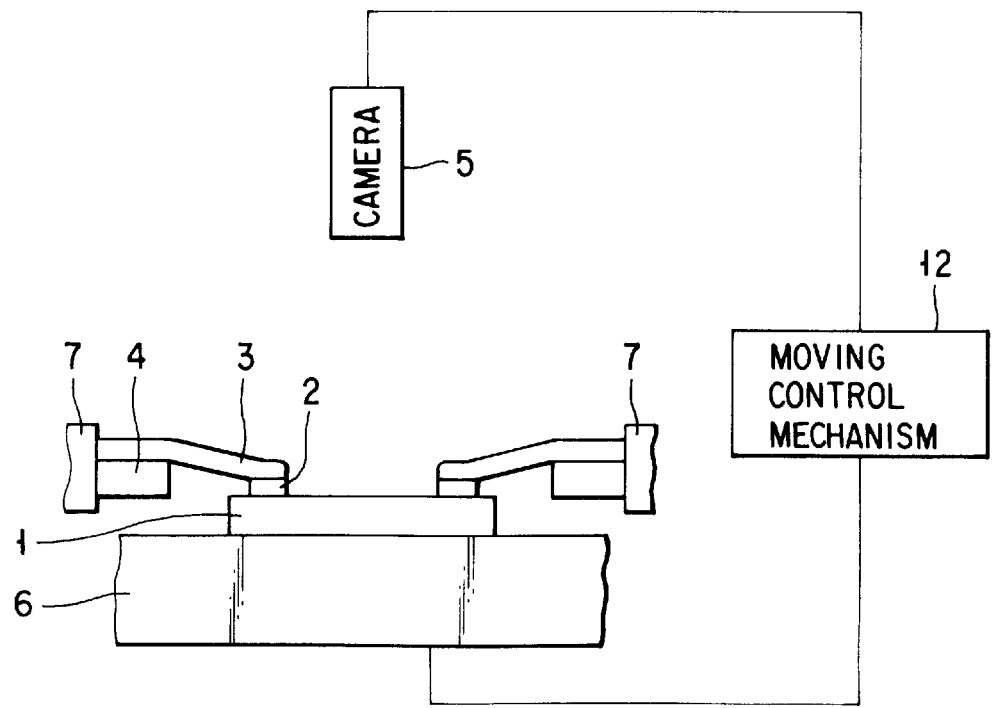
FIG. 17 is a side view of the apparatus for inspecting an LSI device in the assembly process according to application Embodiments 2 and 3.

In Embodiments 2 and 3, the camera is moved by means of the moving control mechanism. Instead of moving the camera itself, the focus may be changed in proportionate to the moving distance of the stage. Alternatively, the stage 6 and the camera 5 may be moved synchronously by means of a common control mechanism 12, as shown in FIG. 17.

As is explained above, according to the present invention, it is possible to detect the slight upward separation of the lead simultaneously with the out of place in position. When the lead having a connection failure is detected, the lead is subjected to the bonding again. If so, it is possible to reduce defective products due to the connection failure, improving assembly yield of an LSI device.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A apparatus for inspecting an LSI device in an assembly process, comprising:

a stage for immobilizing an LSI chip thereon;

an assembly mechanism for controlling a lead so as to be connected to a predetermined portion of said LSI chip;

an image-data receiving mechanism for taking at least two types of image data including a first image data of a lead connection state immediately after said connection is made by said assembly mechanism and a second image data of a lead connection state after at least a portion of said lead is moved to a different position with respect to the LSI chip on the stage.

2. The apparatus according to claim 1, wherein said first and second image data taken by said image-data receiving mechanism are compared to each other to determine whether or not said lead is duly connected to said predetermined portion.

3. The apparatus according to claim 1, wherein said image-data receiving mechanism for receiving said first and second image data include out-of-focus image data.

4. An apparatus for inspecting an LSI device in an assembly process, comprising:

a stage for immobilizing an LSI chip thereon;

a holding portion for holding a plurality of flexible leads;

assembling means for controlling said flexible leads so as to be connected to predetermined portions of said LSI chip;

a camera for taking image data of a connection state between said flexible leads and said predetermined portions connected by said assembling means; and a control mechanism for changing a relative position between said stage and said holding portion in order to inspect said in order to inspect said connection state.

5. The apparatus according to claim 4, wherein said camera takes two image data of connection states before and after the movement of said control mechanism, and said two image data are compared to each other.

6. The apparatus according to claim 4, wherein said control mechanism has a function of moving said stage and said camera synchronously with a predetermined distance apart therebetween.

7. The apparatus according to claim 4, wherein said control mechanism has a function of moving said stage away from said holding portion by a predetermined distance.

8. The apparatus according to claim 4, wherein said control mechanism has a function of moving said stage toward said holding portion by a predetermined distance.

9. The apparatus according to claim 4, wherein said control mechanism has a function of moving said stage and said camera in an upward direction by the same distance.

10. The apparatus according to claim 4, wherein said control mechanism has a function of moving said stage and said camera in a downward direction by the same distance.

11. An apparatus for inspecting an LSI device in an assembly process, comprising:

a stage for immobilizing an LSI chip thereon;

assembling means for controlling a flexible lead so as to be connected to a predetermined portion of said LSI chip;

a camera for taking a connection state of said lead to said predetermined portion in the form of image data; and a moving control mechanism for moving said chip and said camera or only said chip from a first position to a second position while maintaining at least a portion of said lead at the first position.

12. The apparatus according to claim 11, wherein said assembling means includes a holding portion for holding said lead and said holding portion is unmoved and left in said first position even if said chip or camera moved from said first position to second position, by means of said moving control mechanism.

13. The apparatus according to claim 11, wherein a moving distance between said first position and said second position is longer than a depth of focus inherent in said camera.

14. An apparatus for inspecting an LSI device in an assembly process, comprising:

a stage for immobilizing an LSI chip thereon;

assembling means having a holding portion for holding a flexible lead, for controlling said flexible lead so as to be connected to a predetermined portion of said LSI chip;

a camera for providing image data related to the connection state of said lead to said predetermined portion;

a moving control mechanism for setting a distance between said chip and said camera before a movement of said chip and camera to be equal to that set after the movement of said chip and camera while said holding portion is maintained in a position at which said lead is connected to said predetermined portion of said chip by said assembling means;

wherein two types of image data are provided by said camera respectively before and after said moving control mechanism is functioned, and wherein the two types of image data are compared to each other to determine whether or not said lead is duly connected to said predetermined portion of said chip.

15. The apparatus according to claim 14, wherein a distance moved by said moving control mechanism is longer than the depth of focus inherent in said camera.

* * * * *